(12) United States Patent
Terashi et al.

(10) Patent No.: US 11,167,115 B2
(45) Date of Patent: Nov. 9, 2021

(54) MEDICAL GUIDE WIRE AND MANUFACTURING METHOD OF MEDICAL GUIDE WIRE

(71) Applicant: FMD Co., Ltd., Toda (JP)

(72) Inventors: Tsuyoshi Terashi, Toda (JP); Seiji Shimura, Toda (JP)

(73) Assignee: FMD Co., Ltd., Tokyo (JP)

( * ) Notice: Subject to any disclaimer, the term of this patent is extended or adjusted under 35 U.S.C. 154(b) by 198 days.

(21) Appl. No.: 15/665,428

(22) Filed: Aug. 1, 2017

(65) Prior Publication Data

US 2018/0036515 A1    Feb. 8, 2018

(30) Foreign Application Priority Data

Aug. 2, 2016  (JP) .............................. JP2016-161549

(51) Int. Cl.
  *A61M 25/09*    (2006.01)

(52) U.S. Cl.
  CPC ... *A61M 25/09* (2013.01); *A61M 2025/09083* (2013.01); *A61M 2025/09108* (2013.01)

(58) Field of Classification Search
  None
  See application file for complete search history.

(56) References Cited

U.S. PATENT DOCUMENTS

| | | | | |
|---|---|---|---|---|
| 5,910,364 A | * | 6/1999 | Miyata | A61M 25/09 428/375 |
| 2004/0082879 A1 | * | 4/2004 | Klint | A61B 17/12022 600/585 |
| 2007/0249896 A1 | * | 10/2007 | Goldfarb | A61B 1/0014 600/101 |
| 2011/0230862 A1 | * | 9/2011 | Segner | A61M 25/09 604/529 |

(Continued)

FOREIGN PATENT DOCUMENTS

| | | |
|---|---|---|
| JP | H09-056822 A | 3/1997 |
| JP | 2010-214054 A | 9/2010 |
| JP | 2012-179222 A | 9/2012 |

OTHER PUBLICATIONS

Japanese decision to grant a patent dated May 16, 2017.
Japanese notice of the reason for refusal dated Dec. 13, 2016.

*Primary Examiner* — Sean P Dougherty
*Assistant Examiner* — Benjamin S Melhus
(74) *Attorney, Agent, or Firm* — Yokoi & Co., U.S.A.; Toshiyuki Yokoi

(57) ABSTRACT

Conventionally, a coil formed in an irregular shape is used on a distal end side of the coil of a guide wire or a distal joining section is used on the tip of the guide wire to shorten a length in a longitudinal direction of a rigid joint portion for improving the passing performance to the occluded lesion. However, it is not enough especially in the completely occluded lesion. Thus, it is an important technical problem to improve both the passing performance and safety. An (Continued)

2A outer coil having a coil inclined portion and a distal joining section connected with the coil inclined portion are provided on a distal end portion of the guide wire. In the coil inclined portion, each one turn of a coil wire is continuously inclined in a longitudinal direction. Thus, both the passing performance and safety can be remarkably improved especially in the completely occluded lesion.

4 Claims, 7 Drawing Sheets

(56) References Cited

U.S. PATENT DOCUMENTS

| | | | |
|---|---|---|---|
| 2012/0041421 A1* | 2/2012 | Nishigishi | A61M 25/09 604/528 |
| 2014/0358169 A1* | 12/2014 | Terashi | A61B 17/3207 606/159 |

* cited by examiner step D step E

MEDICAL GUIDE WIRE AND MANUFACTURING METHOD OF MEDICAL GUIDE WIRE

CROSS-REFERENCES TO RELATED APPLICATIONS

This patent specification is based on Japanese patent application, No. 2016-161549 filed on Aug. 2, 2016 in the Japan Patent Office, the entire contents of which are incorporated by reference herein.

BACKGROUND OF THE INVENTION

1. Field of the Invention

The present invention relates to a medical guide wire used for treatment of an occluded lesion of a blood vessel or the like and a manufacturing method of the medical guide wire.

2. Description of Related Art

Conventionally, in the treatment of the vascular lesion such as stenosis and the completely occluded lesion of the blood vessel, a coil formed in an irregular shape is used on the distal end side for improving selectivity of the blood vessel at a blood vessel branch part to be reached to the desired lesion. Alternatively, a constant diameter coil having a small outer diameter is used for inserting the coil into a microchannel (or tiny blood vessel) of the completely occluded lesion. Alternatively, a medical guide wire (hereafter, referred to as a guide wire) in which the distal end portion of the core and the distal end portion of the coil are connected to shorten the length in the longitudinal direction of the rigid joint portion is used for making the guide wire reach the lesion. Thus, the vascular lesion is treated by expanding the diameter of the blood vessel.

In the treatment of expanding the diameter of the blood vessel of the occluded lesion, there are two types of treatment methods. One is the treatment method for making the guide wire pass through the completely occluded lesion by increasing the bending rigidity of the distal end portion of the guide wire to increase penetrating performance. The other is the treatment method for making the guide wire pass through the completely occluded lesion by increasing flexibility of the guide wire and using a microchannel.

Recently, it is revealed that there is a microchannel having a pore diameter of approximately 0.250 mm in the completely occluded lesion.

In the above described case, from a viewpoint of avoiding to damage the blood vessel wall and ensuring safety, the treatment method for making the guide wire pass through the completely occluded lesion using the microchannel existed in the completely occluded lesion is earnestly desired.

Patent document 1 discloses a guide wire having a coil formed in an irregular shape at the distal end portion.

Patent document 2 discloses a guide wire having a joint portion at the distal end portion so that the length in the longitudinal direction of the rigid joint portion is shorten.

[Patent document 1] Japanese Patent Laid-Open Publication No. 09-56822

[Patent document 2] Japanese Patent Laid-Open Publication No. 2010-214054

BRIEF SUMMARY OF THE INVENTION

In the guide wire described in Patent document 1, each of continuous turns of the coil spring provided on the distal end portion is formed in an ellipse or an oval shape having the same pitch angle, the same major diameter and the same minor diameter with the other turns. In addition, the inner periphery of the coil wire is connected with the edge of the core material. Thus, the guide wire can be easily bent in a uniaxial direction over the entire length of the coil spring.

In the guide wire described in Patent document 2, by using a joint member made of Au—Sn or the like, the length in the longitudinal direction of the rigid joint portion of the joint portion formed by connecting the distal end of the core wire with the distal end of the coil spring is shorten. Thus, operability is improved in the completely occluded lesion.

Different from the present invention, Patent documents 1 and 2 do not disclose the guide wire including a core and an outer coil provided on the outer side of the core, wherein the outer coil has a coil inclined portion on the distal end side of the outer coil, the coil inclined portion is flat-shaped and each one turn of the coil wire of the coil inclined portion is continuously inclined in one direction of a longitudinal direction with an inclination angle in the coil inclined portion, and a flat-shaped distal joining section is formed by connecting the coil inclined portion with a tip of the core distal end portion. In the present invention, by using the above described configuration, even when the outer coil having the coil outer diameter of 0.014 inch (0.3556 mm) is used, for example, the microchannel having the pore diameter of approximately 0.011 inch (0.2794 mm), which is downsized several degrees from 0.014 inch, can be easily captured and the guide wire can be safely passed through the occluded lesion. Furthermore, Patent documents 1 and 2 do not disclose the technology for enabling the operator to extremely easily grasp the position of the distal end portion of the guide wire in the occluded lesion from the difference of operability caused by the inflow/outflow of living tissue having different properties flew in or out of the large inclined coil groove portion formed between the coil wires of the coil inclined portion or the difference of the amount of the inflow/outflow of the living tissue in accordance with the advancing/retracting of the guide wire.

The above described technologies are important technical problems required for securing the healthy blood flow at the occluded lesion, and for performing the subsequent treatment (e.g., indwelling of the stent). In particular, the above described technologies are required for the guide wire for facilitating to capture the microchannel in the completely occluded lesion and for making the guide wire pass thorough the occluded lesion safely in the treatment of expanding the diameter of the blood vessel.

The present invention provides a guide wire and a manufacturing method of the guide wire for remarkably improving passing performance required for the treatment of the occluded lesion, especially for the treatment of the completely occluded lesion.

A core has a portion gradually tapered in diameter from a proximal end side to a distal end side. The distal end side of a core distal end portion of the core is inserted into an outer coil. A distal joining section is provided on a distal end portion of the outer coil, and a proximal joining section is provided on a proximal end portion of the outer coil. The proximal joining section is connected with the core distal end portion.

The outer coil has a coil inclined portion on the distal end side and has a coil constant diameter portion having a constant outer diameter on the proximal end side. Neighboring portions of a coil wire are in contact with each other in the coil constant diameter portion.

The coil inclined portion is flat-shaped. Each one turn of the coil wire of the coil inclined portion is continuously inclined in one direction of a longitudinal direction with an inclination angle more than a pitch angle of the coil constant diameter portion and less than 80°.

The distal joining section is formed by connecting the coil inclined portion located at the distal end side of the outer coil with a tip of the core distal end portion.

The coil inclined portion has a largely inclined portion with the inclination angle of 35° to 75°.

The largely inclined portion has the inclination angle of 35° to 75°. The inclination angle of the gradually inclined portion is more than the pitch angle of the coil constant diameter portion and equal to or less than the inclination angle of the largely inclined portion.

A vertical cross-sectional area ratio of a vertical cross-sectional area of an inclined coil groove portion of the coil inclined portion with respect to a vertical cross-sectional area of a constant diameter coil groove portion of the coil constant diameter portion is 2.55 to 14.95 in the outer coil. (The vertical cross-sectional area ratio is calculated by dividing the vertical cross-sectional area of the inclined coil groove portion by the vertical cross-sectional area of the constant diameter coil groove portion.)

A manufacturing method of the guide wire, the method comprising: a step of winding and forming a constant diameter coil having a constant outer diameter and a cylindrical shape; a step of arranging a guide line-equipped core distal end portion and the constant diameter coil on linear grooves of a pair of metal dies at a position of forming a coil inclined portion; a step of forming the outer coil having the coil inclined portion by pressing the constant diameter coil while the metal dies are obliquely moved to incline a wound portion of the constant diameter coil; a step of forming the core distal end portion by pulling the guide line of the guide line-equipped core distal end portion located at the distal end side out of a tip of the outer coil and then cutting and removing the guide line; and a step of forming the distal joining section by connecting the coil inclined portion with the tip of the core distal end portion using a bonding member.

A distal joining section is provided on a distal end portion of the outer coil, and a proximal joining section is provided on a proximal end portion of the outer coil. The proximal joining section is connected with the core distal end portion.

The outer coil includes a coil inclined portion on the distal end side and has a coil constant diameter portion having a constant outer diameter on the proximal end side. Neighboring portions of a coil wire are in contact with each other in the coil constant diameter portion.

The coil inclined portion is flat-shaped. Each one turn of the coil wire of coil inclined portion is continuously inclined in one direction of a longitudinal direction with an inclination angle more than (exceeding) a pitch angle of the coil constant diameter portion and less than 80°.

The distal joining section is formed by connecting the coil inclined portion located at the distal end side of the outer coil with a tip of the core distal end portion.

When the flat-shaped distal joining section is formed by connecting the core with the inclined coil, the tiny blood vessel existing in the completely occluded lesion can be easily captured and the guide wire can be safely passed through the tiny blood vessel.

The coil inclined portion includes a largely inclined portion having a large inclination angle at the distal end side and a gradually inclined portion having an inclination angle gradually reducing to the proximal end side.

When the coil inclined portion having the largely inclined portion is connected, distal joining section can be more flatly formed and the tiny blood vessel can be more easily captured in the completely occluded lesion.

Furthermore, when the gradually inclined portion having an inclination angle gradually reducing from the distal end side to the proximal end side is provided, the guide wire can be pushed forward while an inner diameter of the captured tiny blood vessel is gradually expanded. Thus, the passing performance of the guide wire can be significantly improved in the completely occluded lesion.

The largely inclined portion has the inclination angle of 35° to 75°. The inclination angle of the gradually inclined portion is more than the pitch angle of the coil constant diameter portion and equal to or less than the inclination angle of the largely inclined portion.

Consequently, the tiny blood vessel of the completely occluded lesion can be more easily captured and the passing performance to pass through the occluded lesion can be improved.

A vertical cross-sectional area ratio of a vertical cross-sectional area of an inclined coil groove portion of the coil inclined portion with respect to a vertical cross-sectional area of a constant diameter coil groove portion of the coil constant diameter portion is 2.55 to 14.95 in the outer coil. (The vertical cross-sectional area ratio is calculated by dividing the vertical cross-sectional area of the inclined coil groove portion by the vertical cross-sectional area of the constant diameter coil groove portion.)

The operator can extremely easily grasp the position of the distal end portion of the guide wire in the occluded lesion from the difference of operability caused by the inflow/outflow of living tissue having different properties flew in or out of the large inclined coil groove portion formed between the coil wires of the coil inclined portion or the difference of the amount of the inflow/outflow of the living tissue in accordance with the advancing/retracting of the guide wire. Thus, the guide wire is prevented from being mistakenly inserted into the false lumen.

Consequently, the guide wire can be safely passed through the occluded lesion.

A manufacturing method of the medical guide wire, the method comprising: a step of winding and forming a constant diameter coil having a constant outer diameter and a cylindrical shape; a step of arranging a guide line-equipped core distal end portion and the constant diameter coil on linear grooves of a pair of metal dies at a position of forming a coil inclined portion; a step of forming the outer coil having the coil inclined portion by pressing the constant diameter coil while the metal dies are obliquely moved to incline a wound portion of the constant diameter coil; a step of forming the core distal end portion by pulling the guide line of the guide line-equipped core distal end portion located at the distal end side out of a tip of the outer coil and then cutting and removing the guide line; and a step of forming the distal joining section by connecting the coil inclined portion with the tip of the core distal end portion using a bonding member.

When the flat-shaped distal joining section is formed by connecting the core with the coil inclined portion, the guide wire capable of capturing the tiny blood vessel existing in the completely occluded lesion can be manufactured, although the tiny blood vessel is considered to be difficult to be passed through.

Furthermore, the guide wire capable of increasing the amount of the inflow/outflow of living tissue flew in or out of the inclined coil groove portion at the outer peripheral side of the coil inclined portion can be manufactured. Thus, the operator can more easily feel the contact of the distal end portion of the guide wire from the difference of the property of the living tissue. Consequently, the guide wire can be safely passed through the occluded lesion while being prevented from being mistakenly inserted into the false lumen.

BRIEF DESCRIPTION OF THE DRAWINGS

FIG. 5A is an explanation drawing explaining the inclination angle of the largely inclined portion and the vertical cross-sectional area of the inclined coil groove portion. FIG. 5B is an explanation drawing explaining the inclination angle of the coil constant diameter portion and the vertical cross-sectional area of the constant diameter coil groove portion.

FIG. 6 shows the processes A to C in the processes A to E.

FIG. 6 shows the processes D and E in the processes A to E.

DETAILED DESCRIPTION OF THE INVENTION

Hereafter, embodiments of the guide wire and manufacturing method of the guide wire of the present invention will be explained.

Figure 1:
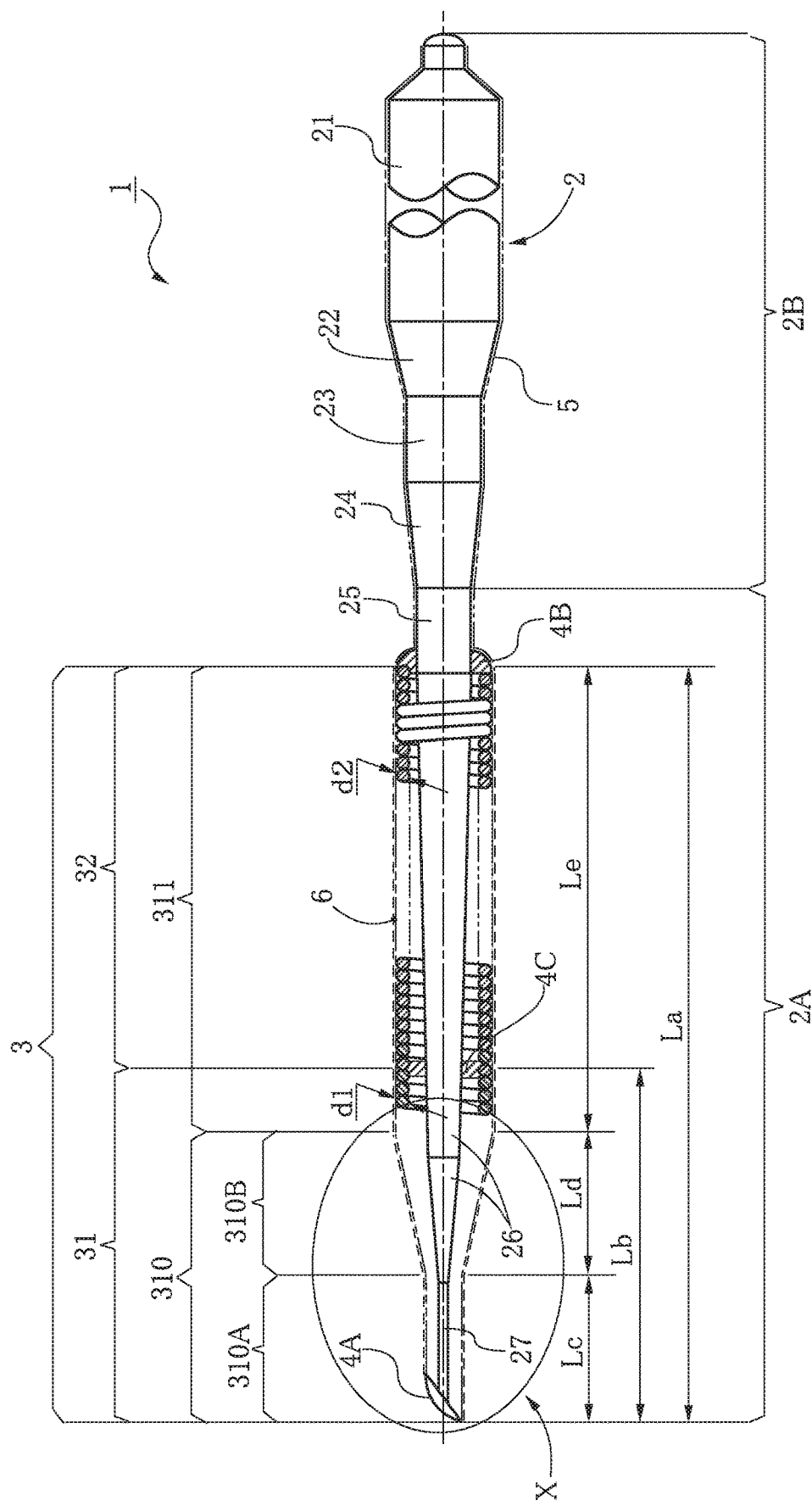
FIG. 1 is a partially cutaway front view showing whole a guide wire concerning the embodiment of the present invention.
Figure 2:
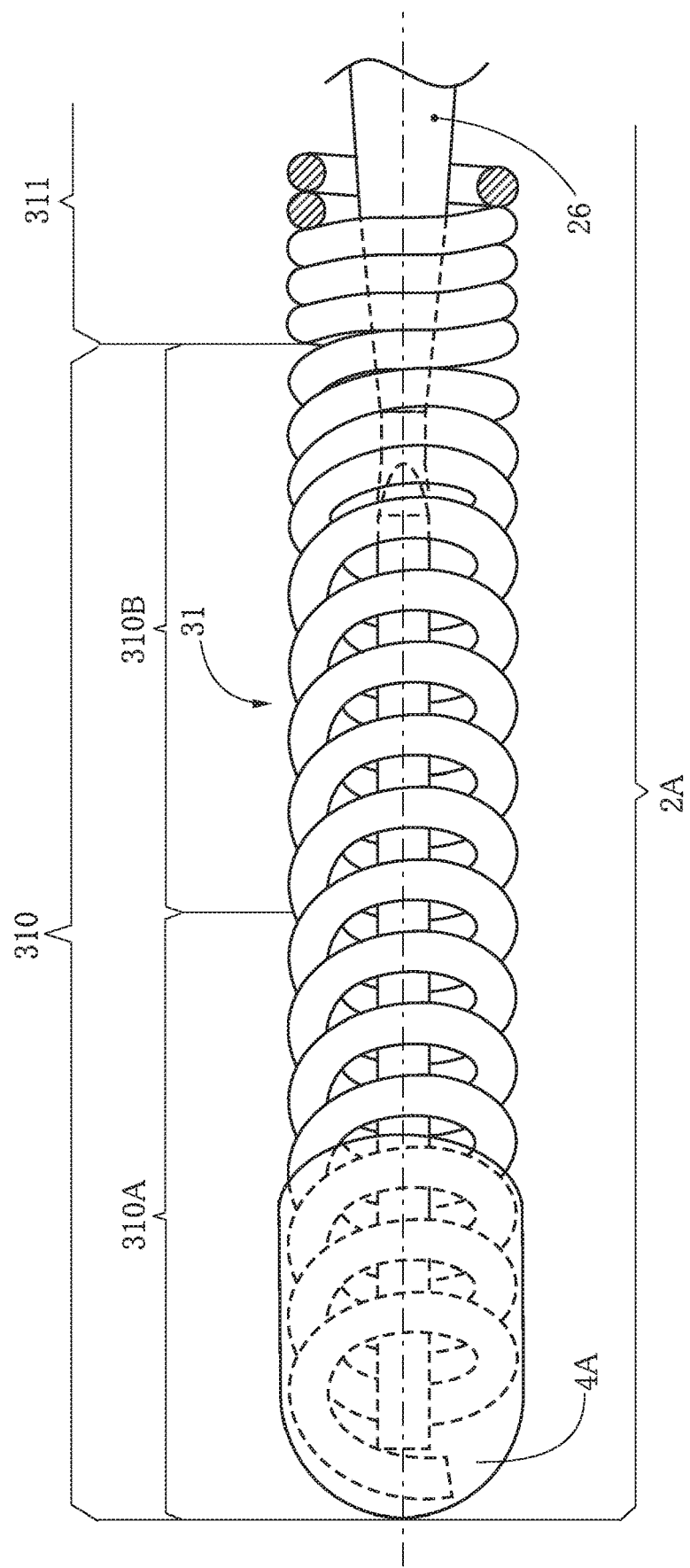
FIG. 2 is an enlarged plan view of a main part of an X part of the distal end side of the guide wire concerning the embodiment of the present invention shown in FIG. 1.
Figure 3:
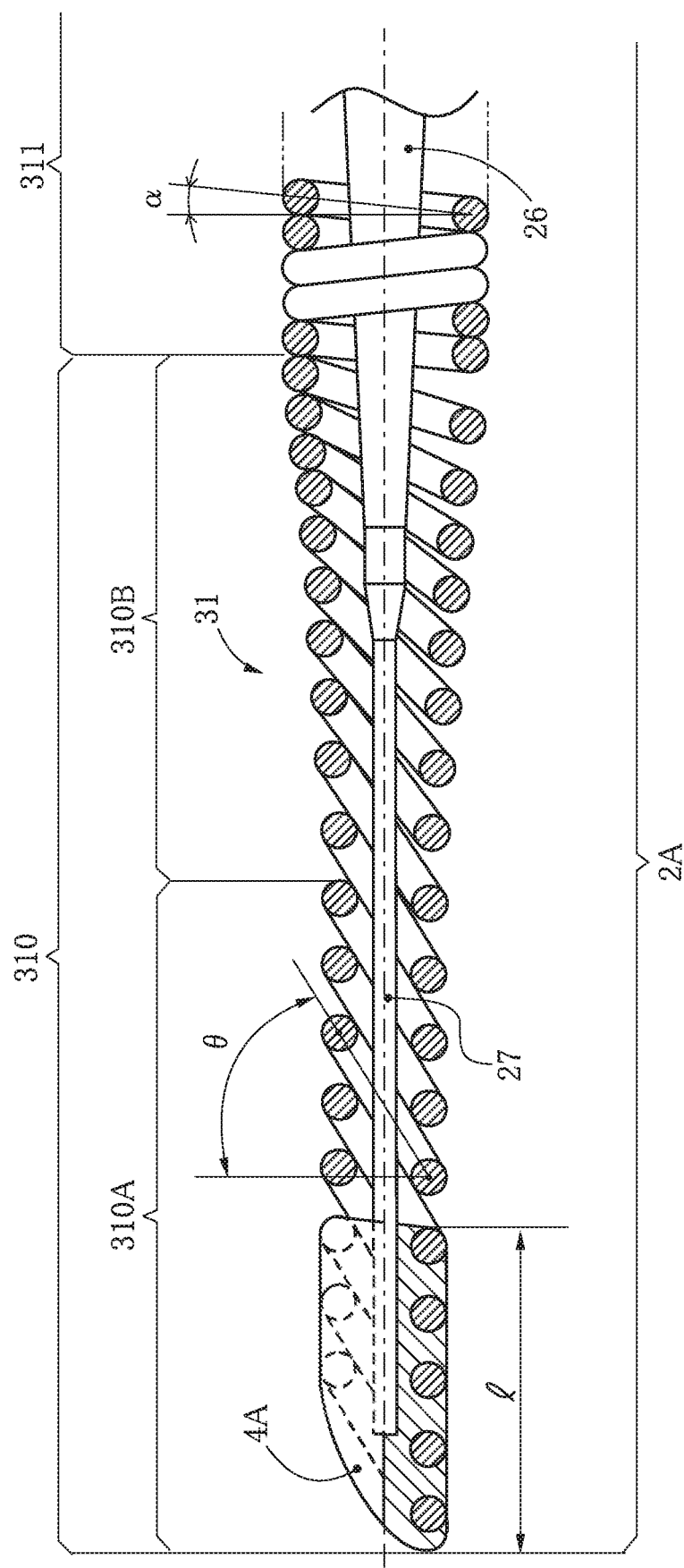
FIG. 3 is an enlarged front view of a main part of the X part of the distal end side of the guide wire concerning the embodiment of the present invention shown in FIG. 1.

FIGS. 1-3 show a guide wire 1 concerning the embodiment of the present invention. FIG. 1 is a front view showing whole the guide wire by omitting an X part located at the distal end side. FIG. 2 shows an enlarged plan view of a main part of the X part omitted in FIG. 1. FIG. 3 shows an enlarged front view of a main part of the X part omitted in FIG. 1.

The guide wire 1 has a core 2, an outer coil 3, a lubricative coating 5 and a hydrophilic coating 6.

The distal end side of a core distal end portion 2A passes through the outer coil 3. A distal joining section 4A is formed by connecting the distal end portion of the outer coil 3 with a tip of the core distal end portion 2A by using a joint member. A proximal joining section 4B is formed by connecting the proximal end portion of the outer coil 3 and proximal end side of the core distal end portion 2A.

A lubricative coating 5 is formed on an outer periphery of the proximal end side of the core distal end portion 2A and an outer periphery of a core proximal end portion 2B using fluorine resin or the like.

A hydrophilic coating 6 is formed on an outer periphery of the outer coil 3 using hydrophilic substance such as polyvinylpyrrolidone and maleic anhydride. Note that the guide wire 1 of the present invention has an extremely small diameter relative to its length. Therefore, the guide wire 1 is partially exaggerated or omitted in drawings because it is difficult to illustrate the guide wire 1 in a specified area if the same scaling is used for horizontal and vertical directions.

The core 2 is formed by the core proximal end portion 2B and the core distal end portion 2A. The core proximal end portion 2B includes a first constant diameter portion 21, a first tapered portion 22, a second constant diameter portion 23, and a second tapered portion 24 in order from the proximal end side to the distal end side. The core distal end portion 2A includes a third constant diameter portion 25, a combined truncated cone 26 formed by connecting two truncated cones, and a distal small-diameter body 27 from the proximal end side to the distal end side.

The outer diameter of the core 2 is gradually reduced from the proximal end side to the distal end side approximately in a range of 0.3556 mm (0.014 inch) to 0.065 mm. The entire length of the core 2 is approximately 2900 mm. The distal small-diameter body 27 has a length of 14 mm and has a rectangular cross-sectional shape. In order to secure excellent insertion property and assemblability in the later described coil inclined portion 310 (especially in a largely inclined portion 310A), the cross-sectional shape is preferably rectangular rather than circular. In the present embodiment, a rectangular shape having a thickness t of 0.04 mm and a width S of approximately 0.083 mm (shown in FIG. 4) is formed by press-working the distal small-diameter body 27 having a circular cross-sectional shape and an outer diameter of 0.065 mm.

The core 2 is made from a stainless steel wire, a Ni—Ti alloy wire or the like. For example, as shown in Japanese Patent Laid-Open Publication No. 2002-69586, the stainless steel wire having high strength manufactured by repeating a wire drawing process and an annealing process is used. In addition, as shown in Japanese Patent Laid-Open Publication No. 2002-069555, a Ni—Ti alloy wire manufactured by thermal processing under certain conditions is used.

The core 2 can be formed by welding and joining different kinds of wires between the core distal end portion 2A and the core proximal end portion 2B. For example, the core distal end portion 2A can be the Ni—Ti alloy wire and the core proximal end portion 2B can be the stainless steel wire.

The outer coil 3 has a first outer coil 31 at the distal end side and has a second outer coil 32 at the proximal end side. A length La of the longitudinal direction of the outer coil 3 is 150 mm, for example. The first outer coil 31 and the second outer coil 32 are screwed to each other at the end portion and connected with each other at a middle joining section 4C using a joint member. Instead of the screw fitting, the coil wires can be connected with each other by welding, for example.

The first outer coil 31 is formed by winding a radiopaque wire to form a coil having a length Lb of 40 mm in the longitudinal direction and the later described outer diameter, for example. A wire diameter d1 of the radiopaque wire is 0.060 mm, for example. The radiopaque wire is, for example, made of gold, platinum, tungsten, nickel-containing gold, nickel-containing platinum, or doped tungsten formed by adding doping agent (e.g., K, Al, Si) to tungsten.

A wire diameter d2 of the second outer coil 32 is 0.060 mm, for example. The second outer coil 32 is formed by winding a radiopaque wire made of a stainless steel or the like.

A constant diameter portion 311 is formed by a coil wire so that neighboring portions of the coil wire are in contact with each other. A length Le of the coil constant diameter portion 311 in the longitudinal direction is 130 mm, for example. In the coil constant diameter portion 311, 110 mm (La–Lb) of the proximal end side is the second outer coil 32. The second outer coil 32 is formed by a coil having the later described outer diameter. Note that 20 mm of the distal end side of the coil constant diameter portion 311 is a distal end portion of the first outer coil 31. The first outer coil 31 is formed by a coil wire made of the radiopaque wire. Here, "neighboring portions of the coil wire are in contact with each other" means not only the state that the neighboring portions of the coil wire are completely in contact with each other (in line contact with each other over the entire circumference of the coil wire) but also the state that the neighboring portions of the coil wire are in contact with each other so that clearance between the neighboring portions of the coil wire cannot be visually confirmed.

FIG. 2 and FIG. 3 show enlarged views of a main part of an X part of the distal end side of the guide wire shown in FIG. 1. FIG. 2 shows an enlarged plan view of the main part of the X part of the distal end side. FIG. 3 shows an enlarged front view of the main part of the X part of the distal end side. The same reference numerals are used for the same components. In addition, the hydrophilic coating 6 is omitted.

In FIG. 2 and FIG. 3, the first outer coil 31 includes the coil inclined portion 310 having a length of 20 mm in the longitudinal direction and the coil constant diameter portion 311 having a length of 20 mm in the longitudinal direction in order from the distal end side to the proximal end side.

The coil inclined portion 310 includes a largely inclined portion 310A on the distal end side and a gradually inclined portion 310B on the proximal end side. The largely inclined portion 310A has a length Lc (shown in FIG. 1) of 10 mm in the longitudinal direction and has the maximum inclination angle, for example. The gradually inclined portion 310B has a length Ld (shown in FIG. 1) of 10 mm in the longitudinal direction, for example. The inclination angle of the gradually inclined portion 310B is gradually reduced to the proximal end side.

The inclination angle of the coil inclined portion 310 is more than a pitch angle α (shown in FIG. 3) of the coil constant diameter portion 311 and less than 80°.

When the later described flat-shaped distal joining section 4A is formed, the tiny blood vessel existing in the completely occluded lesion can be easily captured and the guide wire can be safely passed through the completely occluded lesion.

Figure 5A:
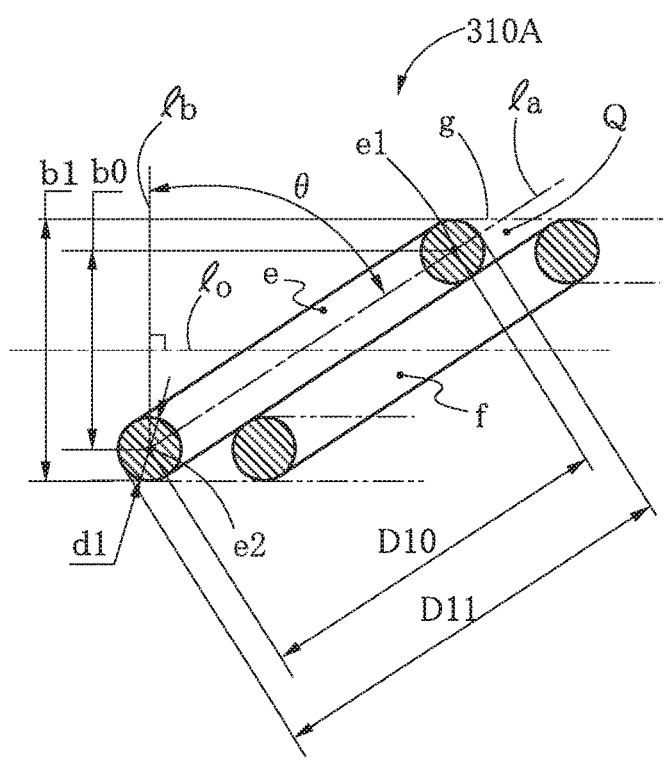
FIGS. 5A and 5B are explanation drawings for explaining an inclination angle of the coil inclined portion and the coil constant diameter portion shown in FIG. 3 and a vertical cross-sectional area ratio of the groove portion formed between the coil wires.
Figure 5B:
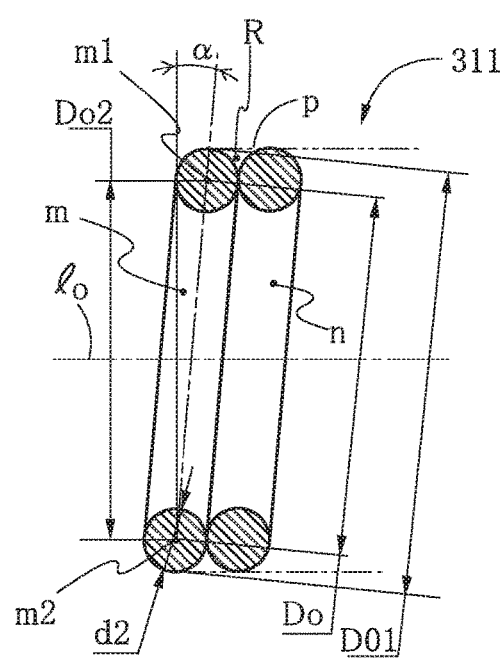

Here, the inclination angle of the coil inclined portion 310 will be explained using FIGS. 5A and 5B. FIG. 5A is an explanation drawing explaining, for example, the inclination angle of the largely inclined portion 310A of the coil inclined portion 310 shown in FIG. 3. FIG. 5B is an explanation drawing explaining, for example, the pitch angle α of the coil constant diameter portion 311 shown in FIG. 3.

In the present invention, "coil inclined portion" means a flat-shaped coil wire where each one turn of the coil wire is continuously inclined in one direction of the longitudinal direction (one direction along the center line of the coil in the longitudinal direction) with an inclination angle. In the present invention, "inclination angle of the coil inclined portion" means an acute angle sandwiched by the center line of one turn of the inclined coil wire (material) and a vertical line perpendicular to the center line of the coil wire.

More specifically, in the vertical cross-sectional view (FIG. 5A) of the longitudinal direction along a minor axis of the coil inclined portion 310 (cut by a plane perpendicular to a major axis of the coil inclined portion 310), "inclination angle of the coil inclined portion" means an acute angle θ sandwiched by a center line la of one turn of the coil wire and a vertical line lb perpendicular to a center line lo of the coil of the coil inclined portion 310. Here, the center line la is formed by connecting a center point e1 of a circular cross section of one side of the coil wire and a center point e2 of a circular cross section of the other side.

Specifically, in the present embodiment, a coil outer diameter D11 of one turn of the coil wire of the largely inclined portion 310A is 0.3556 mm (0.14 inch) and the wire diameter d1 is 0.060 mm. Thus, a length D10 of the major diameter between the center points of one turn of the coil wire is 0.2956 mm. When a minor axis diameter b1 is 0.2195 mm, a length bo of the minor diameter between the center points of the coil is 0.1595 mm.

Here, the inclination angle θ can be expressed by the following relational expression (1)

$$\cos\theta = bo/D10 \quad (1)$$

Thus, when the inclination angle θ is calculated by using the relational expression (1), the inclination angle θ of the largely inclined portion 310A is approximately 57.3°.

In the same manner as described above, when the pitch angle α of the coil constant diameter portion 311 is calculated by using FIG. 5B, a coil outer diameter D01 of the coil constant diameter portion 311 of one turn of the coil wire is 0.3556 mm (0.014 inch), the wire diameter d2 is 0.060 mm, and therefore a center diameter Do of the one turn of the coil wire is 0.2956 mm, same as described above.

Since the center diameter Do of one turn of the coil wire is 0.2956 mm, an average diameter Do2 of the coil is approximately 0.2941 mm (a square root of ($0.2956^2 - 0.03^2$)).

When the above described relational expression (1) is used, the pitch angle α of the coil constant diameter portion 311 is approximately 5.8°. Since the technical concept is different between the general coil spring (e.g., push/pull spring) having a constant outer diameter and the inclined coil of the present invention, the definition of the pitch angle used in the general coil spring is newly defined as "inclination angle of the coil inclined portion" in the coil inclined portion of the present invention.

Next, by using FIG. 4 with reference to FIGS. 3 and 5, the distal joining section 4A formed by connecting the coil inclined portion 310 with the largely inclined portion 310A will be explained.

A length l of the longitudinal direction of the distal joining section 4A is 0.50 mm to 1.00 mm (FIG. 3). In FIG. 4, the distal joining section 4A formed by using eutectic alloy as a joint member is melted and fixed while the joint member is inserted between the coil wires and into the coil. Thus, an outer diameter b1 of the distal joining section 4A in the minor axis direction is 0.2195 mm, same as the minor axis diameter b1 shown in the above described FIG. 5A.

A major axis diameter a1 is 0.3556 mm, same as the coil outer diameter D11 shown in the above described FIG. 5A. Accordingly, the distal joining section 4A shown in FIG. 4 which is the left side view of FIG. 3 (the guide wire 1 is viewed from the distal end side) is formed in an elliptic shape having the minor axis diameter b1 of 0.2195 mm and the major axis diameter a1 of 0.3556 mm.

Figure 4:
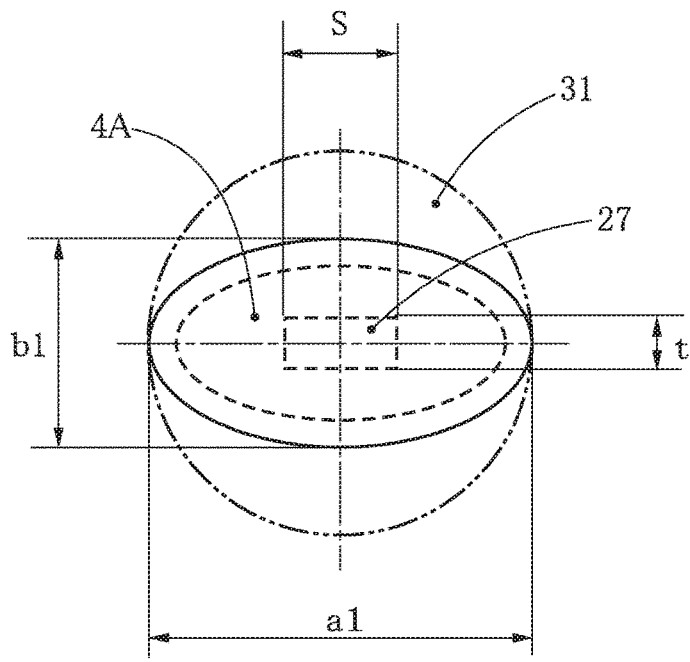
FIG. 4 is an enlarged left side view of a main part of the distal joining section of the guide wire in the embodiment shown in FIG. 3.

Here, when a diameter do of a circular shape having the area equal to the area of the elliptic shape of the distal joining section 4A shown in FIG. 4 is calculated, the minor axis diameter of the elliptic shape is b1, the major axis diameter is a1, and therefore the relation between the area of the elliptic shape and the area of the circular shape having the area equal to the elliptic shape can be expressed by the following relational expression (2)

$$a1 \times b1 = do^2 \qquad (2)$$

When the diameter do is calculated by using the relational expression (2) while the major axis diameter a1 is 0.3556 mm and the minor axis diameter b1 is 0.2195 mm, the diameter do of the circular shape is approximately 0.2794 mm (0.011 inch).

This means that the diameter do of the circular shape having the area equal to the elliptic shape of the distal joining section 4A shown in FIG. 4 is approximately 0.2794 mm (0.011 inch).

Namely, although the coil having the coil outer diameters (D01, D11) of 0.014 inch is used, when the coil is inclined and the distal joining section 4A connected with the inclined coil is formed in the elliptic shape as shown in FIG. 4, the diameter do of the circular shape having the area equal to the elliptic shape is 0.011 inch.

Accordingly, by using the guide wire 1 having the distal joining section 4A of the present invention, even when the coil outer diameter of the first outer coil 31 is 0.014 inch, the tiny blood vessel having the pore diameter of approximately 0.011 inch, which is downsized several degrees, can be passed through.

When the distal joining section 4A passes through the tiny blood vessel, the distal joining section 4A gradually passes from the tipmost end. For example, when the distal joining section 4A passes from the tipmost end to the position having an area of half of the elliptic shape of the distal joining section 4A shown in FIG. 4, same as described above, a diameter do1 of the circular shape having the area equal to the area of half of the elliptic shape is calculated by using the relational expression (2) and the diameter do1 is approximately 0.1976 mm (approximately 0.00778 inch).

When the tip of the distal joining section 4A passes to the position having the area of half of the elliptic shape, the tiny blood vessel having the pore diameter of up to 0.1976 mm (approximately 0.00778 inch) can be easily captured by using the first outer coil 31 with the coil having the coil outer diameters (D01, D11) of 0.3556 mm (0.014 inch).

Accordingly, the distal joining section 4A of the present invention easily captures the entrance of the tiny blood vessel of the completely occluded lesion by the tipmost end of the flat-shaped portion, passes the tiny blood vessel having the pore diameter of up to approximately 0.1976 mm at the position where the cross-sectional area of the distal joining section 4A becomes approximately half, and passes the tiny blood vessel having the pore diameter of up to approximately 0.2794 at the position where the cross-sectional area of the distal joining section 4A becomes approximately maximum. This is because the tiny blood vessel is formed of the later described living tissue and therefore the tiny blood vessel is easily elastically deformed.

As a supplemental explanation, when the coil inclined portion 310 like the present invention is formed by using the coil having the coil outer diameter of smaller than 0.3556 mm and the distal joining section 4A connected with the coil inclined portion 310 is used, the distal joining section 4A can pass through the tiny blood vessel having further smaller pore diameter.

For example, when the coil outer diameter of 0.010 inch (0.254 mm) shown in Japanese Patent Laid-Open Publication No. 2010-214054 (Patent document 2) is used, the inclination angle of the coil inclined portion 310 of the embodiment of the present invention is set to 57.3° and the pore diameter do of the circular shape having the area equal to the area of the elliptic shape of the flat-shaped distal joining section 4A is calculated from the above described relational expressions (1) and (2), the pore diameter do is approximately 0.2045 mm (approximately 0.008 inch).

Namely, when the configuration same as the embodiment of the present invention is prepared by using the coil having the coil outer diameter of 0.010 inch which is smaller than 0.014 inch, the guide wire can pass through the tiny blood vessel up to approximately 0.008 inch which is smaller than 0.011 inch.

The inclination angle θ of the largely inclined portion 310A of the coil inclined portion 310 connected with the distal joining section 4A is preferably 35° to 75°, more preferably 40° to 70° and further more preferably 45° to 65°.

If the inclination angle θ is below the above described lower limit value, the minor axis diameter b1 of the elliptic shape of the distal joining section 4A becomes large and it is difficult to pass the guide wire through the tiny blood vessel. If the inclination angle θ is more than the above described upper limit value, when the largely inclined portion 310A is connected with the tip of the distal small-diameter body 27 to form the distal joining section 4A, it is difficult to increase the outer diameter of the distal small-diameter body 27 inserted into the coil inclined portion 310 and difficult to increase the bending rigidity of the distal small-diameter body 27.

As a supplemental explanation, in the case of the embodiment of the present invention, the minor axis diameter b1 is 0.2195 mm and the wire diameter d1 is 0.060 mm, and therefore a coil inner diameter of the largely inclined portion 310A is 0.0995 mm (0.2195−0.06×2) at the minor axis side.

Accordingly, since the thickness t of the distal small-diameter body 27 is 0.04 mm in the embodiment of the present invention, the distal small-diameter body 27 can be sufficiently inserted into the coil inner diameter (0.0995 mm) of the minor axis side. Thus, excellent insertion property and assemblability can be secured.

The gradually inclined portion 310B is provided on the proximal end side of the largely inclined portion 310A of the coil inclined portion 310. The inclination angle of the coil is gradually reduced to the proximal end side in the gradually inclined portion 310B. The inclination angle of the gradually inclined portion 310B is more than the pitch angle α (approximately 5.8° in the present embodiment) of the coil constant diameter portion 311 and equal to or less than the inclination angle of the largely inclined portion 310A.

The entrance of the tiny blood vessel is captured by the tipmost end of the flat-shaped portion of the distal joining section 4A connected with the largely inclined portion 310A and guided into the tiny blood vessel. Then, the guide wire 1 is pushed forward while the inner diameter of the tiny blood vessel is gradually expanded by the gradually inclined portion 310B. Thus, the passing performance of the distal end portion of the guide wire 1 is further improved.

Next, by using FIG. 5 with reference to FIGS. 2 and 3, the vertical cross-sectional area ratio of each groove portion formed between the coil wires will be explained.

FIG. 5A is the explanation drawing explaining the inclination angle of the largely inclined portion 310A of the coil inclined portion 310 and the explanation drawing of an inclined coil groove portion Q formed between the coil wires of the largely inclined portion 310A.

FIG. 5B is an explanation drawing explaining the pitch angle α of the coil constant diameter portion 311 and the explanation drawing of a constant diameter coil groove portion R formed between the contacted neighboring portions of the coil wire in the coil constant diameter portion 311.

FIG. 5A is a vertical cross-sectional view of the largely inclined portion 310A of the coil inclined portion 310 in the longitudinal direction along the minor axis diameter b1 (cut by a plane perpendicular to the major axis of the largely inclined portion 310A).

Here, "the vertical cross-sectional area ratio of each groove portion formed between the coil wires" means a vertical cross-sectional area ratio of a vertical cross-sectional area of the inclined coil groove portion Q formed between outer peripheral lines of two neighboring portions of the coil wire of the largely inclined portion 310A of the coil inclined portion 310 with respect to a vertical cross-sectional area of the constant diameter coil groove portion R formed between outer peripheral lines of two contacted neighboring portions of the coil wire of the coil constant diameter portion 311 in the vertical cross-sectional shape of the longitudinal direction along the minor axis diameter b1 of the coil inclined portion 310. (The vertical cross-sectional area ratio is calculated by dividing the vertical cross-sectional area of the inclined coil groove portion Q by the vertical cross-sectional area of the constant diameter coil groove portion R.)

The inclined coil groove portion Q means an approximate arrowmark shaped groove portion surrounded by a virtual outer shape line (reference numeral g) indicated by two-dot chain line and outer peripheral lines of two neighboring turns of the coil wire (reference numerals e, f) in FIG. 5A. Here, the virtual outer shape line (reference numeral g) is formed by extending a dimension indication line showing the minor axis diameter b1 of two neighboring turns (reference numerals e, f) of the coil wire in the longitudinal direction.

The constant diameter coil groove portion R means an approximate delta shaped groove portion surrounded by a virtual outer shape line (reference numeral p) indicated by two-dot chain line and the outer peripheral lines of two contacted neighboring portions (reference numerals m, n) of the coil wire in FIG. 5B. Here, the virtual outer shape line (reference numeral p) is formed by extending an outer shape line showing an outer shape of two contacted neighboring portions (reference numerals m, n) of the constant diameter coil in the longitudinal direction.

In FIG. 5A, when the vertical cross-sectional area of the inclined coil groove portion Q of the largely inclined portion 310A in the embodiment of the present invention is calculated by using the enlarged drawing and so on, the vertical cross-sectional area is approximately 0.001887 $mm^2$.

Similarly, in FIG. 5B, when the vertical cross-sectional area of the constant diameter coil groove portion R of the coil constant diameter portion 311 in the embodiment of the present invention is calculated, the vertical cross-sectional area is approximately 0.000387 $mm^2$.

The vertical cross-sectional area ratio of the vertical cross-sectional area of the inclined coil groove portion Q with respect to the vertical cross-sectional area of the constant diameter coil groove portion R is approximately 4.88. (The vertical cross-sectional area ratio is calculated by dividing the vertical cross-sectional area of the inclined coil groove portion Q by the vertical cross-sectional area of the constant diameter coil groove portion R.)

Considering the practical range of the present invention, the vertical cross-sectional area ratio is preferably 2.55 to 14.95, and more preferably 2.94 to 14.95. (The vertical cross-sectional area ratio is calculated by dividing the vertical cross-sectional area of the inclined coil groove portion Q by the vertical cross-sectional area of the constant diameter coil groove portion R.)

If the vertical cross-sectional area ratio is below the above described lower limit value, the operator hardly feel the difference of the property of the hand operation caused by the later described difference of the property of the living tissue flew in or out of the groove portions between the turns of the coil wire in the occluded lesion. Thus, the operator hardly recognize the position of the distal end portion of the guide wire in the occluded lesion.

If the vertical cross-sectional area ratio exceeds the above described upper limit value, the inclined coil groove portion Q is expanded and increased in the longitudinal direction. Thus, while high flexibility can be obtained in the coil inclined portion 310, the bending rigidity is deteriorated and property to push forward is deteriorated.

Next, the living tissue in the occluded lesion will be explained.

In the occluded lesion, organization of blood clot is advanced and the blood clot is replaced with fibrous tissue. Then, calcification is advanced by deposition of calcium salt or the like to harden the occluded lesion. The organization is fast at both end portions of the occluded lesion and slow at the center portion.

It is known that the tiny blood vessel having the pore diameter of approximately 0.250 mm is formed in the advancing process of the organization of the blood clot.

It is also known that rough and rugged feeling is transferred to the hand side of the operator when the distal end of the guide wire is located in the intima, and sticking feeling is transferred to the hand side of the operator when the distal end of the guide wire is located in the media.

The operator normally moves the distal end portion of the guide wire 2 mm to 3 mm forward and backward, and the forward/backward operation is repeated to prevent the distal end portion of the guide wire from being mistakenly inserted into the false lumen (other than true lumen). Thus, the operator makes the operation to insert the distal end portion into the true lumen which is the vascular lumen to be really treated. In such a case, it is an important issue for the operator making the hand operation to grasp the position of the distal end portion of the guide wire in the occluded lesion.

In the guide wire 1 of the present invention, the outer coil 3 has the coil inclined portion 310, and the largely inclined portion 310A of the coil inclined portion 310 has the inclined coil groove portion Q. The vertical cross-sectional area of the inclined coil groove portion Q is 4.88 times greater than the vertical cross-sectional area of the constant diameter coil groove portion R of the coil constant diameter portion 311.

The living tissue of the occluded lesion flows in or out of the inclined coil groove portion Q having large cross-sectional area corresponding to the forward/backward operation of the operator (normally moved forward/backward 2 mm to 3 mm).

Because the living tissue flows in or out of the inclined coil groove portion Q having large cross-sectional area, rough and rugged feeling can be easily transferred to the operator when the distal end of the guide wire 1 is located in the intima, and sticking feeling can be easily transferred to the operator when the distal end of the guide wire 1 is located in the media.

Because of this, the operator can extremely easily grasp the position of the distal end portion of the guide wire in the blood vessel wall of the occluded lesion. Consequently, the operator can make the operation safely while the distal end portion of the guide wire is prevented from being mistakenly inserted into the false lumen.

In the advancing process of the organization at the both end portions of the occluded lesion, a periphery of the pore diameter is hardened by calcification to form hard tiny blood vessel when the organization is advanced. On the other hand, the periphery of the pore diameter is atheromatous to form relatively soft the tiny blood vessel when the organization is during advancing. Thus, both the hard tiny blood vessel and the relatively soft the tiny blood vessel are scattered.

In such a case, the guide wire 1 of the present invention captures the entrance of the tiny blood vessel by the tipmost end of the flat-shaped distal joining section 4A regardless of the hard or soft state of the periphery of the tiny blood vessel. Then, after the largely inclined portion 310A of the outer coil 3 enters in the tiny blood vessel, the guide wire is pushed forward while the inner diameter of the tiny blood vessel is gradually increased by the gradually inclined portion 310B. Thus, the passing performance in the tiny blood vessel of the occluded lesion can be easily increased.

Furthermore, as the method of inserting the guide wire into the completely occluded lesion in the occluded lesion, retrograde approach operation is known as the percutaneous coronary angioplasty method as shown in Japanese Patent Laid-Open Publication No. 2012-152362.

In the completely occluded lesion, the hard tiny blood vessel is located at the proximal end portion which is one of the both end portions of the lesion (end of the lesion near the side where the blood flows rapidly and directly). In the hard tiny blood vessel, the calcification of the blood clot is quick and the blood clot is easily hardened.

On the other hand, the relatively soft tiny blood vessel is located at the distal end portion (opposite to the proximal end portion). In the relatively soft tiny blood vessel, the calcification of the blood clot is slow and the blood clot is in the semi-hardened state.

The retrograde approach operation is an operation of inserting the guide wire from distal end portion by focusing on the fact that the relatively soft tiny blood vessel is located at the distal end portion of the completely occluded lesion.

As the problem of such a case, in order to insert the guide wire from the distal end portion of the completely occluded lesion, the guide wire should be inserted into the largely bent portion having large curvature and meandering (such as collateral circulation called as corkscrew).

The guide wire 1 of the present invention can easily capture the tiny blood vessel by the flat-shaped distal joining section 4A. In addition, he distal end portion (especially in the largely inclined portion 310A) of the outer coil 3 is flat-shaped together with the distal joining section 4A. Furthermore, the distal small-diameter body 27 arranged inside the largely inclined portion 310A is a flat-shaped rectangle in cross-section having the flat direction same as the flat direction of the largely inclined portion 310A. Consequently, excellent operability can be achieved by the bi-directionality of high flexibility in the minor axis diameter b1 side and low flexibility in the major axis diameter a1 side.

Namely, in the guide wire 1 of the present invention, by using the fact that the operability is bi-directional, the inserting operation (such as an operation of changing moving direction using the difference of flexibility) becomes easy in the blood vessel. In particular, the guide wire can be easily inserted into the collateral circulation which is the largely bent portion having large curvature and meandering.

Furthermore, as described above, the guide wire 1 of the present invention captures the tiny blood vessel easily regardless of the hard or soft state of the periphery of the tiny blood vessel. In addition, since the passing performance in the tiny blood vessel is further increased, the guide wire 1 of the present invention has special functions and effects available for a wide range of operations.

Next, the manufacturing method of the guide wire 1 having the distal joining section 4A connected with the coil inclined portion 310 concerning the present invention will be explained.

Figure 6:
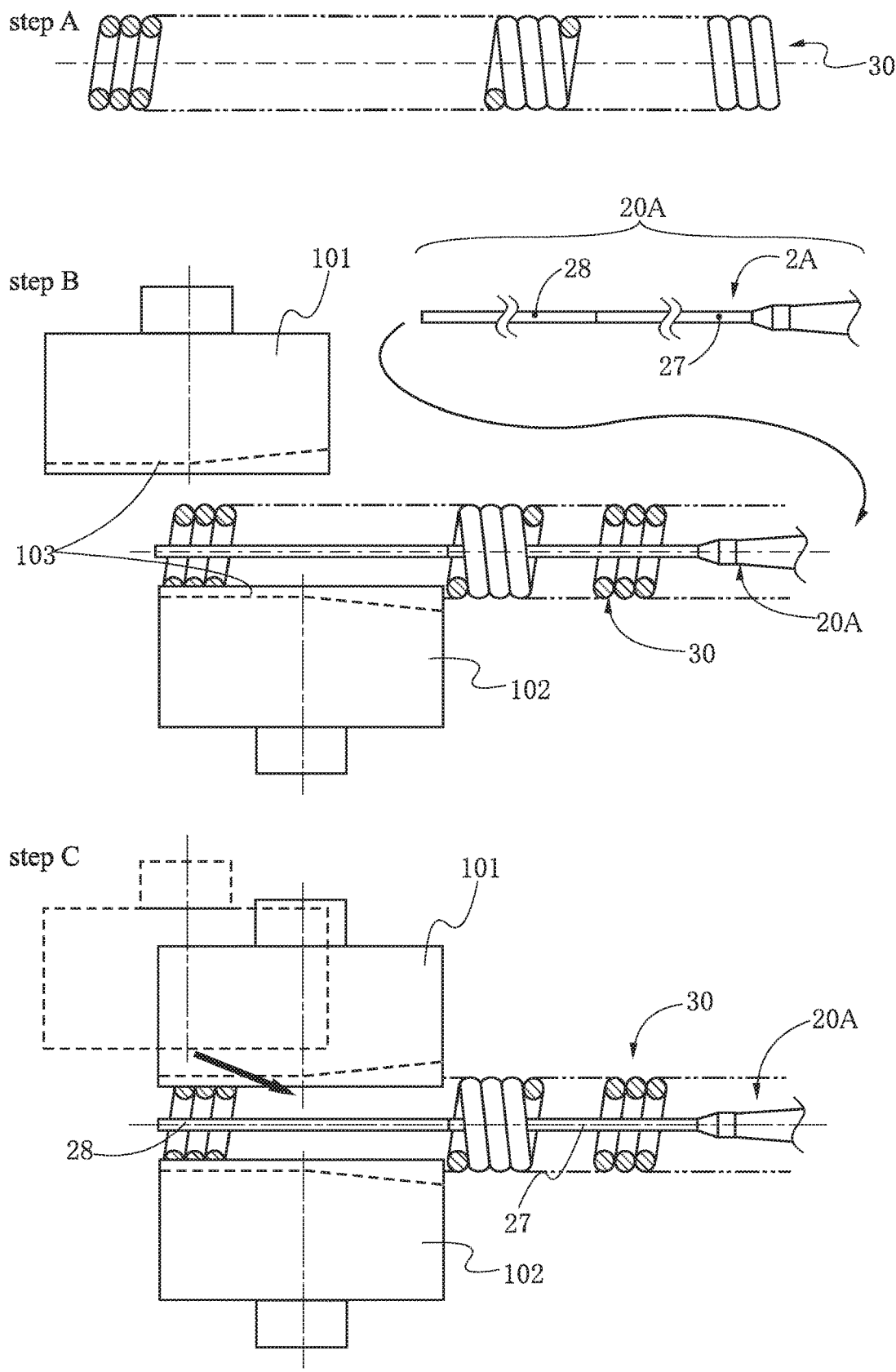
FIG. 6 is a process drawing showing a manufacturing method of the guide wire concerning the embodiment of the present invention.
Figure 7:
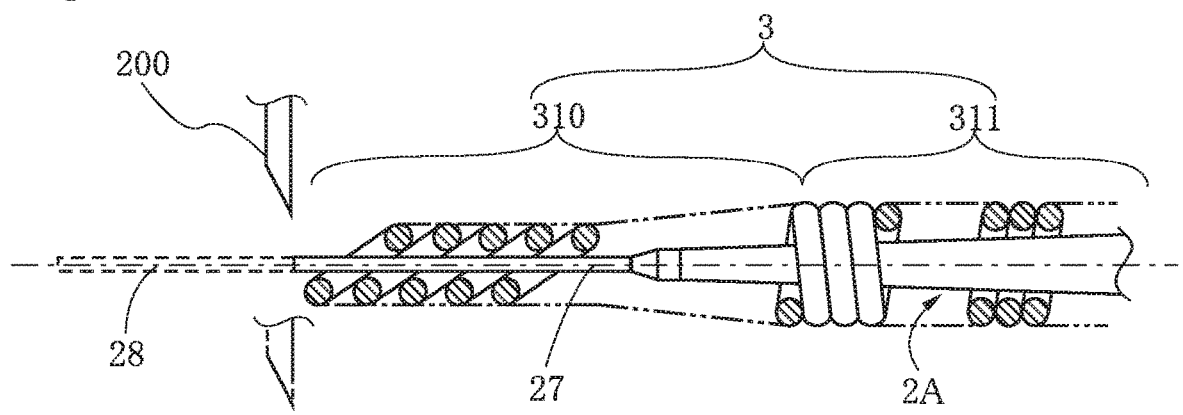
FIG. 7 is a process drawing showing a manufacturing method of the guide wire concerning the embodiment of the present invention.
Figure 7:
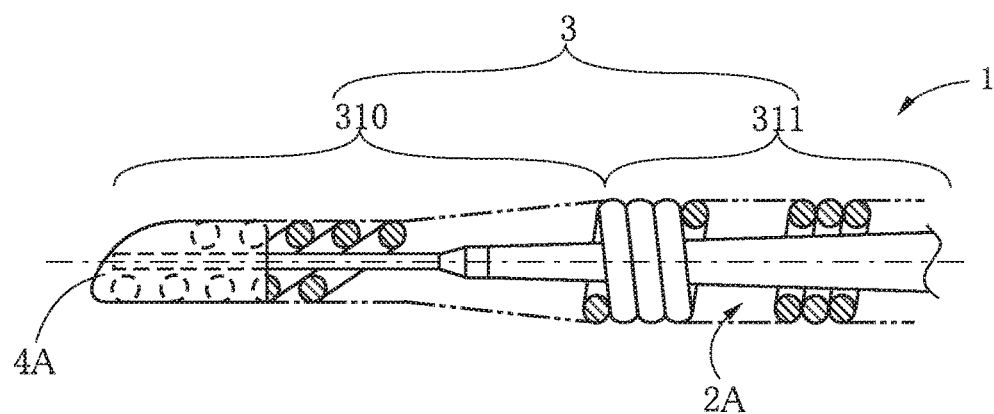

FIGS. 6 and 7 are drawings showing the manufacturing method of the guide wire 1 concerning the embodiment of the present invention. FIG. 6 shows the processes A to C in the processes A to E of the manufacturing method of the guide wire 1 of the present invention. FIG. 7 shows the processes D and E in the processes A to E of the manufacturing method of the guide wire 1 of the present invention.

Figure 8A:
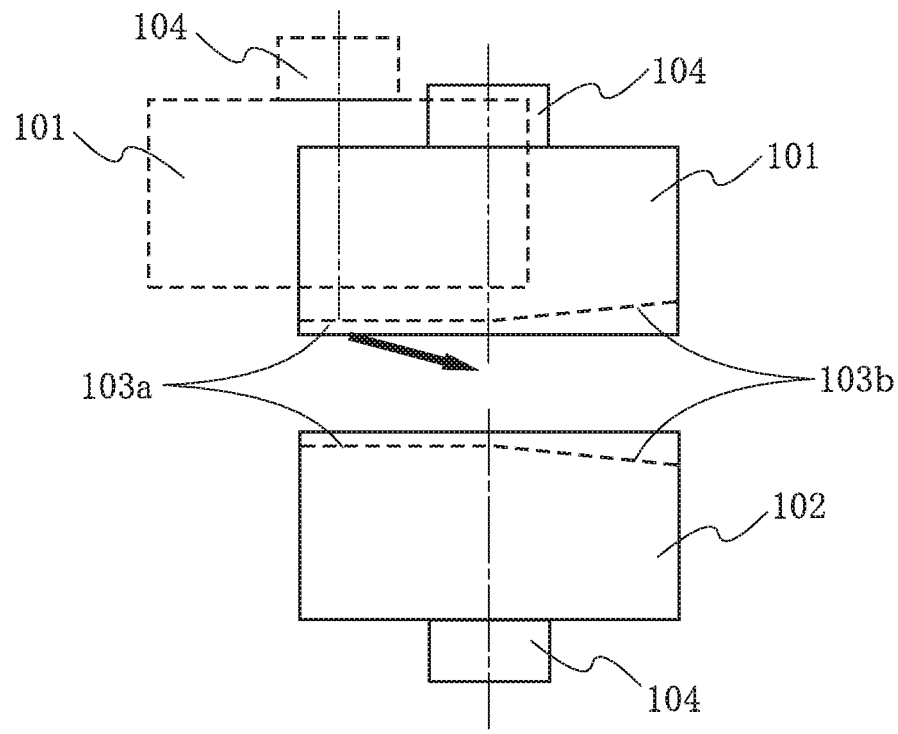
FIGS. 8A to 8C are die drawings for manufacturing the coil inclined portion of the guide wire concerning the embodiment of the present invention.
Figure 8B:
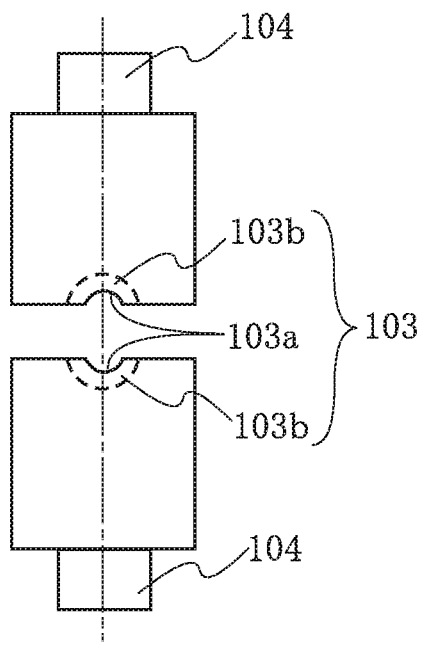
Figure 8C:
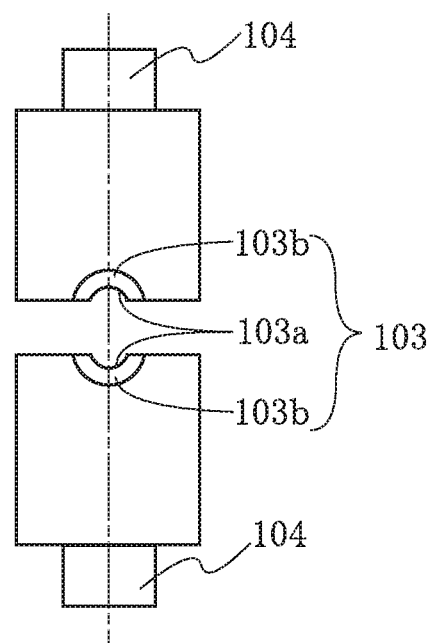

FIGS. 8A to 8C are die drawings (a pair of upper and lower dies) for manufacturing the coil inclined portion 310 of the guide wire 1 concerning the embodiment of the present invention.

In FIGS. 6 and 7, the manufacturing method of the guide wire 1 of the embodiment of the present invention includes: a step (step A) of winding and forming a constant diameter coil 30 having a constant outer diameter and a cylindrical shape; a step (step B) of inserting a guide line-equipped core distal end portion 20A having a guide line 28 at the distal end side of the core distal end portion 2A into the constant diameter coil 30, and arranging the guide line-equipped core distal end portion 20A and the constant diameter coil 30 on linear grooves 103 of an upper die 101 and a lower die 102 (corresponding to "a pair of metal dies" of the present invention) at a position of forming the coil inclined portion 310; a step (step C) of forming the outer coil 3 having the coil inclined portion 310 by pressing the constant diameter coil 30 while one or both of the upper die 101 and the lower die 102 (only the upper die 101 in the present embodiment) is obliquely moved (right obliquely downward arrow direction in the figure, i.e., direction obliquely crossing the center line) with respect to a center line of the constant diameter coil 30 to incline a wound portion of the constant diameter coil 30; a step (step D) of forming the core distal end portion 2A by pulling the guide line 28 of the guide line-equipped core distal end portion 20A out of a tip of the outer coil 3 and then cutting and removing the guide line 28; and a step (step E) of forming the distal joining section 4A by connecting the coil inclined portion 310 located at the distal end side of the outer coil 3 with the tip of the core distal end portion 2A using a bonding member.

When the flat-shaped distal joining section 4A connected with the coil inclined portion 310 of the outer coil 3 is formed, the guide wire 1 capable of easily capturing the tiny blood vessel existing in the occluded lesion can be manufactured although the tiny blood vessel is considered to be difficult to be passed through. In addition, the guide wire 1 is capable of increasing the amount of the inflow/outflow of living tissue flew in or out of the large inclined coil groove portion Q formed between the coil wires of the coil inclined portion 310. Thus, the operator can more easily feel the contact from the difference of the property of the living tissue. Consequently, the guide wire can be safely passed through the occluded lesion while being prevented from being mistakenly inserted into the false lumen.

The guide line 28 is formed for preventing the damage of the distal small-diameter body 27 caused by the pressing when forming the coil inclined portion 310. The guide line 28 can be joined by welding or bonding the same material with the distal small-diameter body 27 or the different materials from the distal small-diameter body 27. Alternatively, the guide line 28 can be formed by extending the distal small-diameter body 27 to the distal end side.

Although the distal joining section 4A can be joined by welding on a plurality of turns of the coil wire located at the distal end side of the coil inclined portion 310 by using a laser welding machine or the like, the distal joining section 4A is preferably joined by using a eutectic alloy from the view point of sealability and safety.

For the eutectic alloy, gold-tin based alloy material having a melting temperature of 210° C. to 450° C. and silver-tin based alloy material having a melting temperature of 220° C. to 470° C.

When forming the distal joining section 4A of the present invention, even if the coil inclined portion 310 of the outer coil 3 exists only in the joint portion forming the distal joining section 4A, such a configuration is included in the present invention. In the step (step E in FIG. 7) of forming the distal joining section 4A, the configuration is defined as "forming the distal joining section 4A by connecting the coil inclined portion 310 of the outer coil 3 with the tip of the distal end portion 2A using a bonding member." However, as another embodiment, the configuration can be also defined as "forming the distal joining section 4A by connecting (only) with the coil inclined portion 310 of the outer coil" without connecting with the tip of the core distal end portion 2A.

Because of this, the guide wire having higher flexibility corresponding to the symptom of the lesion can be obtained.

FIGS. 8A to 8C are a pair of die drawings of the upper die 101 and lower die 102 for manufacturing the coil inclined portion 310 of the outer coil 3.

In FIGS. 8A to 8C, FIG. 8A shows the front view, FIG. 8B shows the left side view of FIG. 8A, and FIG. 8C shows the right side view of FIG. 8A.

The upper die 101 and the lower die 102 have a pair of linear grooves 103. The linear grooves 103 has a linear groove 103a formed on the half of the total length and an inclined linear groove 103b formed on the other part. The linear groove 103a is small to correspond to the portion of the minor axis diameter b1 (for the largely inclined portion 310A). The inclined linear groove 103b corresponds to the portion where the diameter is gradually increased to the proximal end side (for forming the gradually inclined portion 310B).

The guide line-equipped core distal end portion 20A and the constant diameter coil 30, which are arranged on the linear grooves 103, are pressed while the upper die 101 is obliquely moved (left obliquely downward arrow direction in the figure) with respect to the center line of the constant diameter coil 30 to form the largely inclined portion 310A by the small diameter linear groove 103a and form the gradually inclined portion 310B by the inclined linear groove 103b. Thus, the coil inclined portion 310 is formed.

Consequently, the outer coil 3 having the coil inclined portion 310 can be manufactured. When the inclination angle of the coil inclined portion 310 is constant (the gradually inclined portion 310B is not formed), the linear grooves 103 can have a constant groove diameter over the entire length.

As a supplemental explanation, in the guide wire having the outer coil including the coil inclined portion concerning the present invention, in order to further increase the flexibility, clearance having the size of 0.1 to 4.0 times greater than the wire diameter of the coil wire can be formed between neighboring portions of the coil wire without being in line contact or point contact with each other.

As shown in Japanese Patent Laid-Open Publication No. 2015-47451, the guide wire can have an inner coil on the inside of the outer coil and the coil inclined portion can be formed on one or both of the outer coil and the inner coil.

In the above described embodiment, the major axis diameter a1 and the minor axis diameter b1 of the largely inclined portion 310A is constant in the axial direction. However, the largely inclined portion 310A can be formed in the tapered shape, for example, so that the major axis diameter a1 and the minor axis diameter b1 are gradually reduced to the tip. The above described shape can be formed by pressing a conical coil by using the above described method.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A medical guide wire, comprising:
a core that has a portion tapered in diameter from a proximal end side to a distal end side; and
an outer coil into which the distal end side of a core distal end portion of the core is inserted, wherein
a distal joining section is provided on a distal end portion of the outer coil and a proximal joining section is provided on a proximal end portion of the outer coil, the distal joining section being connected with the core distal end portion,
the outer coil includes a coil inclined portion on the distal end side,
the distal joining section includes the coil inclined portion;
the coil inclined portion is flat-shaped having a first minor axis and a first major axis when the coil inclined portion is viewed from the distal end side along a direction extending a center line of the outer coil, and each one turn of the coil wire of the coil inclined portion is continuously inclined in one direction along a center line of the outer coil, the distal joining section is formed by connecting the coil inclined portion with a tip of the core distal end portion by a joint member, the distal joining section having an elliptic shape having a second minor axis and a second major axis when the distal joining section is viewed from the distal end side along the direction extending the center line of the outer coil, a direction of the first minor axis in the flat-shaped coil inclined portion is same as a direction of the second minor axis in the distal joining section when the coil inclined portion and the distal joining section are viewed from the distal end side along the direction extending the center line of the outer coil, and a direction of the first major axis in the flat-shaped coil inclined portion is same as a direction of the second major axis in the distal joining section when the coil inclined portion and the distal joining section are viewed from the distal end side along the direction extending the center line of the outer coil.

2. The medical guide wire according to claim 1, wherein the outer coil includes a coil constant diameter portion having a constant outer diameter on the proximal end side of the coil inclined portion, neighboring portions of a coil wire being in contact with each other in the coil constant diameter portion, the coil inclined portion includes a first inclined portion at the distal end side and a second inclined portion having an inclination angle reducing to the proximal end side, and an inclination angle of the coil inclined portion is more than a pitch angle of the coil constant diameter portion and less than 80°.

3. The medical guide wire according to claim 2, wherein the first inclined portion has the inclination angle of 35° to 75°, and the inclination angle of the second inclined portion is more than the pitch angle of the coil constant diameter portion and equal to or less than the inclination angle of the first inclined portion.

4. A manufacturing method of the medical guide wire according to claim 1:

a step of winding and forming a constant diameter coil having a constant outer diameter and a cylindrical shape;

a step of inserting a guide line-equipped core distal end portion having a guide line at the distal end side of the core distal end portion into the constant diameter coil, and arranging the guide line-equipped core distal end portion and the constant diameter coil on linear grooves of a pair of metal dies at a position of forming the coil inclined portion;

a step of forming the outer coil having the coil inclined portion by pressing the constant diameter coil while one or both of the pair of metal dies is obliquely moved with respect to a center line of the constant diameter coil to incline a wound portion of the constant diameter coil;

a step of forming the core distal end portion by pulling the guide line of the guide line-equipped core distal end portion out of a tip of the outer coil and then cutting and removing the guide line; and a step of forming the distal joining section by connecting the coil inclined portion located at the distal end side of the outer coil with the tip of the core distal end portion using a bonding member.

* * * * *